United States Patent [19]
Mansfield

[11] 4,261,197
[45] Apr. 14, 1981

[54] PROBE FOR THE ULTRASONIC INSPECTION OF MOLTEN ALUMINUM

[75] Inventor: Thomas L. Mansfield, Louisa, Va.

[73] Assignee: Reynolds Metals Company, Richmond, Va.

[21] Appl. No.: 74,798

[22] Filed: Sep. 12, 1979

[51] Int. Cl.³ ............................................. G01N 29/02
[52] U.S. Cl. ....................................... 73/61 R; 73/644
[58] Field of Search ............... 73/61 R, 597, 599, 627, 73/629, 632, 644

[56] References Cited
U.S. PATENT DOCUMENTS
3,444,726  5/1969  Young et al. .......................... 73/61 R FOREIGN PATENT DOCUMENTS
562729  6/1977  U.S.S.R. ..................................... 73/597

OTHER PUBLICATIONS
"Ultrasonic Examination of Liquid Metal", British Aluminum Co., Ltd., Research Laboratories Interim Report No. R. L. 63/8 by Young et al., [1963].

*Primary Examiner*—James J. Gill
*Attorney, Agent, or Firm*—Glenn, Lyne, Girard & McDonald

[57] ABSTRACT

A special probe for the ultrasonic inspection of molten aluminum is described.

7 Claims, 3 Drawing Figures

PROBE FOR THE ULTRASONIC INSPECTION OF MOLTEN ALUMINUM

FIELD OF THE INVENTION

This invention relates to the application of ultrasonic waves to the inspection of molten aluminum. More particularly, it relates to an improved probe for conducting ultrasonic waves between a transducer device and an aluminum melt as part of a molten aluminum inspection process.

BACKGROUND OF THE INVENTION

Ultrasonic waves have become of great importance in recent years. Their unique properties have been applied to industry, signaling, medicine and many other fields.

The use of ultrasonic waves to inspect molten aluminum is known, though not yet widely practiced commercially.

It is known, for example, that molten aluminum can be inspected with ultrasonic waves of relatively high frequencies (1–10 MHz) and low power (0.004–0.04 watts). The most practical means of inspection is the pulse-echo method wherein an ultrasonic wave pulse is transmitted into the molten aluminum and the pulse reflections or echoes are detected and measured. Melt quality can be characterized in terms of the number and amplitude of the echoes reflected from discontinuities such as insoluble melt constituents, attenuations in pulse amplitude, pulse velocity through the melt, and shifts in the ultrasonic wave frequency.

Other applications of ultrasonic waves to the inspection of molten aluminum are of course possible.

For details concerning the implementation of ultrasonic wave technology generally, see B. Carlin, *Ultrasonics*, McGraw-Hill Book Company, Inc., New York-Toronto-London (1960), the disclosure of which is hereby incorporated herein by reference.

To transmit or receive ultrasonic waves to or from an aluminum melt, it is common to use an electromechanical transducer device for converting electrical energy to mechanical energy and vice versa. The most popular electromechanical conversion systems rely either on magnetostriction or the piezoelectric effect to operate. However, magnetostrictive transducers are not generally used for inspecting molten aluminum because of their characteristic low operating frequency (e.g. 60 KHz or less).

Piezoelectric transducers typically have the capability to both transmit and receive ultrasonic waves. Thus a single piezoelectric transducer may be used to perform both functions, or separate transducers may be used for transmitting and receiving. Piezoelectric transducers can readily be made to handle high frequencies and low power levels, and are accordingly well suited for molten aluminum inspection methods.

A transducer can conveniently be coupled to the melt using a probe, sometimes called a "delay line" or a "mechanical standoff". See, for example, U.S. Pat. No. 3,444,726 to R. S. Young et al. The probe serves to isolate the transducer from the high melt temperatures, which will usually run in the range of about 675° to 825° C., and to introduce a time delay between a transmitted pulse and echoes from inclusions located near where the pulse first enters the melt.

The probe will usually be in the form of a bar or rod, one end of which will be immersed in the melt and is known as the "working tip". And the other probe end is coupled to the transducer. Typical probes have previously consisted of a 2 foot long, 1 inch diameter rod, for example, with a water jacket attached to the transducer probe end for cooling.

It has been said that an ideal probe material should have the following properties:

(a) The material should have a constant low acoustic energy attenuation over the range of working temperatures at the frequencies used.

(b) It should be sound and homogeneous and have good resistance to thermal and mechanical shock.

(c) It should have a good resistance to attack by the molten metal. Any material which has the effect of reacting with the molten metal to form a protective film has the disadvantage that wetting of the immersed transmitting end of the probe by the molten metal will be materially reduced.

(d) It should have a low thermal conductivity.

(e) The acoustic impedance, i.e. the product of density and the velocity of sound, should be of the same order as of the molten metal.

Apparently no material has been found which would fulfill all of these requirements.

Sintered rods made from titanium diboride and titanium carbide mixtures in 70/30 and 60/40 volumetric proportions have, for example, been examined by the prior art. With these rods, difficulty was encountered initially in obtaining rods of adequate soundness and in wetting the immersed ends of the rods to allow transmission of ultrasonic energy between the liquid aluminum and the probes. In attempts to effect wetting, the probes were immersed in the liquid aluminum under an inert atmosphere or argon. These attempts were not successful, even when the probe ends were capped with brazing metal before immersion. Greater success was obtained when the rods were capped with pure aluminum at high temperatures (e.g. 1200° C.) under vacuum; these gave low attenuation and a very small loss of signal at the probe-aluminum interfaces. However, these benefits were lost when the probes were removed from the liquid metal and exposed to atmosphere. The probe end surfaces apparently oxidized so that on reimmersion full wetting did not occur and only a small proportion of the available signal was then transmitted into the metal.

A titanium alloy, Ti 317, containing 5% Al and 2.5% Sn (by weight) and obtainable with a single phase structure, was also examined by the prior art and found to resist erosion to a considerable extent. Material having a duplex (Δ+B) structure had a very high attenuation, so that it was only possible to transmit signals up to 2.5 MHz through a 2 ft.×1 in. diameter rod. When converted to a single phase structure, it had a reasonable attenuation, though still higher than desirable. Also, experiments show that titanium does not become wetted until it has been immersed in molten aluminum for approximately thirty minutes.

After looking at titanium diboride titanium carbide sinters and metallic titanium alloys as probe materials, at least one group came to prefer steel (0.26 wt.% carbon content) coated with a sprayed water-suspended Foseco Dycote 34 and tipped with a cap of silver solder. The silver solder accelerated the wetting so that the probes transmitted and received the available energy after approximately three minutes immersion. Once wetted, the probes could be removed from the liquid metal, allowed to cool and then replaced without undue loss of coupling efficiency. And the sprayed refractory coating prevented wetting of the sides of the probes and the introduction of stray vibrations into the liquid metal. It was a problem, however, that the steel tended to be dissolved in the aluminum melt. The problem was tolerated by observing the amplitude of the reflected echoes, and when the amplitude fell to a predetermined level, the probes were removed, shortened and resoldered.

Hence, of various probe constructions that the prior art had looked at, each was affected by one or more of the following problems: wetting did not occur at all or only until the passage of some substantial amount of time after the probe was initially immersed in the melt; wetting did not occur after the probe was removed from the melt, exposed to the atmosphere and cooled, and then re-immersed; at operating temperatures, the probe material attenuated the ultrasonic signals to an undesirable degree; or the probe material was not chemically stable in molten aluminum.

In methods which involve the use of ultrasonic waves for the non-destructive testing of solid materials, it has been known to use a single delay line and a single transducer to both transmit and receive ultrasonic signals.

However in U.S. Pat. No. 3,444,726 to R. S. Young et al, which relates to the ultrasonic inspection of molten aluminum, there is a teaching of using multiple delay lines and multiple transducers. One delay line is coupled to a transducer for transmitting signals, and a second delay line is coupled to a second transducer for receiving the signal echoes. The transmitted signals are bounced off of a detached reflective surface which is immersed in the melt, and the resultant echoes are received. Use of this setup requires accurate measurement of the distances of the reflective surface to the probes, and probe alignment is critical. Also, the setup is not conveniently movable from one spot to another within the melt.

It was against the foregoing background that this invention was made.

INVENTION SUMMARY

This invention is directed to an improved probe for conducting ultrasonic mechanical energy between a transducer device and an aluminum melt in a process of inspecting molten aluminum.

The probe comprises a body member made essentially of titanium, exhibiting preferably a single phase structure. The body member has first and second opposite ends, each of which has a substantially flat end surface which is substantially perpendicular to the body member's longitudinal axis. The first such end forms a working tip for the probe, where the working tip is about ⅛ to 3 inches in length. Preferably, the probe working tip is about ¼ to 2 inches in length. The body member is also defined by a lateral portion adjacent the working tip, where such lateral portion defines a cooling zone for the probe.

The probe further comprises cooling means, such as a water jacket or the like, for extracting heat at the probe cooling zone. The cooling means has the capacity to cool the probe in a manner such that when the working tip reaches a thermal equilibrium upon being immersed in an aluminum melt at a temperature in the range of about 675° to 825° C., there exists a negative temperature gradient of at least 200° C./in along the body member's longitudinal axis within the probe cooling zone, and the temperature of the above-mentioned second body member end is maintained at 300° C. or less.

Preferably, the probe includes a substantially flat reflector surface which is attached as part of the probe in opposed, spaced apart substantially parallel relationship with the above-mentioned substantially flat end surface of the first body member end.

One advantage of this probe is that it is especially adapted for use as a self-contained transmitter-receiver unit in a pulse-echo method of inspecting molten aluminum. A second probe for transmitting or receiving the ultrasonic signals is not required.

Another advantage is that by reason of its special geometry, titanium may be used as the probe material without adverse signal attenuation effects.

A third advantage is that the problems associated with having to align multiple probes are not encountered.

A still further advantage is that the probe is adapted to be readily moved from location to location in the melt with no substantial interruption in the inspection process.

DESCRIPTION OF THE PRESENTLY PREFERRED EMBODIMENTS

Figure 1:
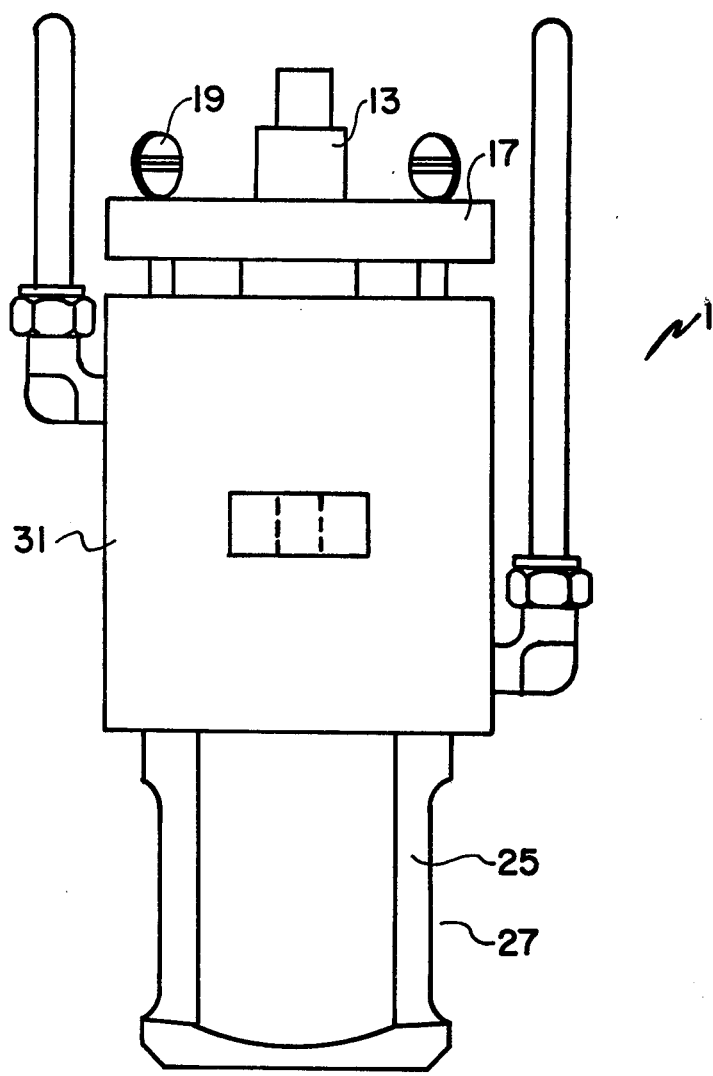
FIG. 1 is a side view of a special molten aluminum inspection probe described herein.
Figure 2:
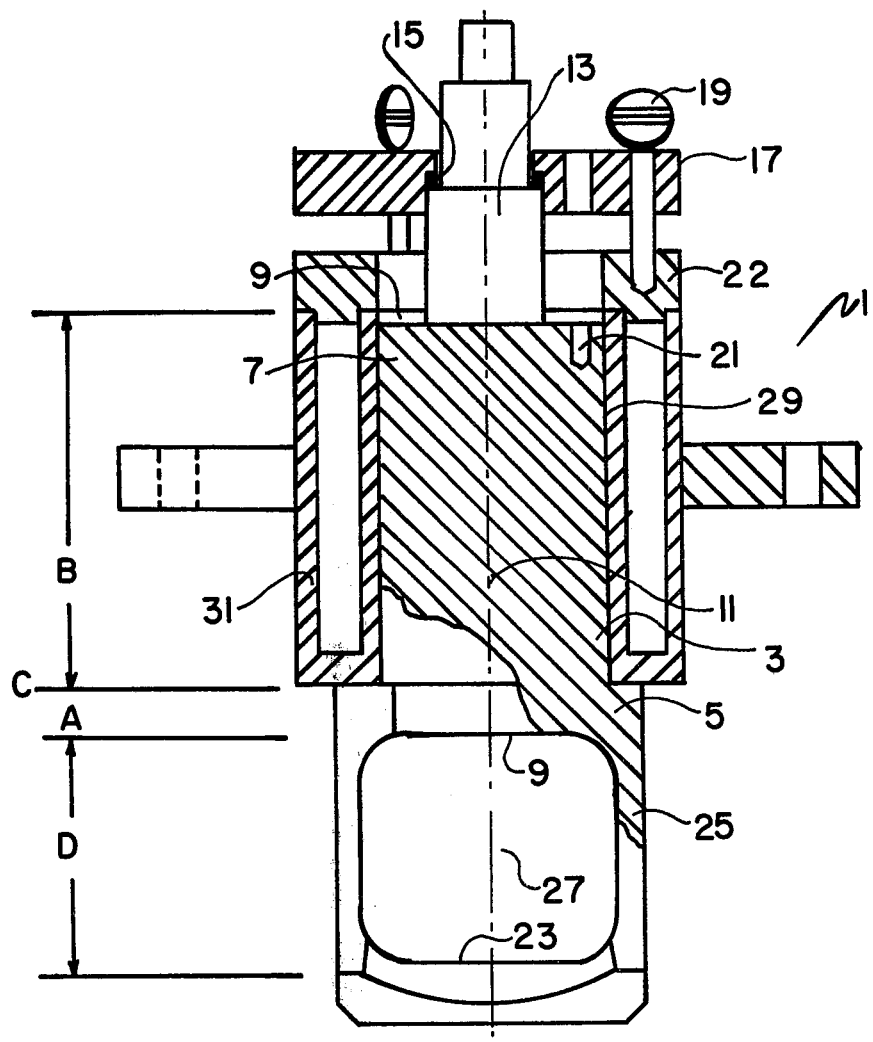
FIG. 2 is a front view of the probe shown in FIG. 1, with sections removed and sections broken away.
Figure 3:
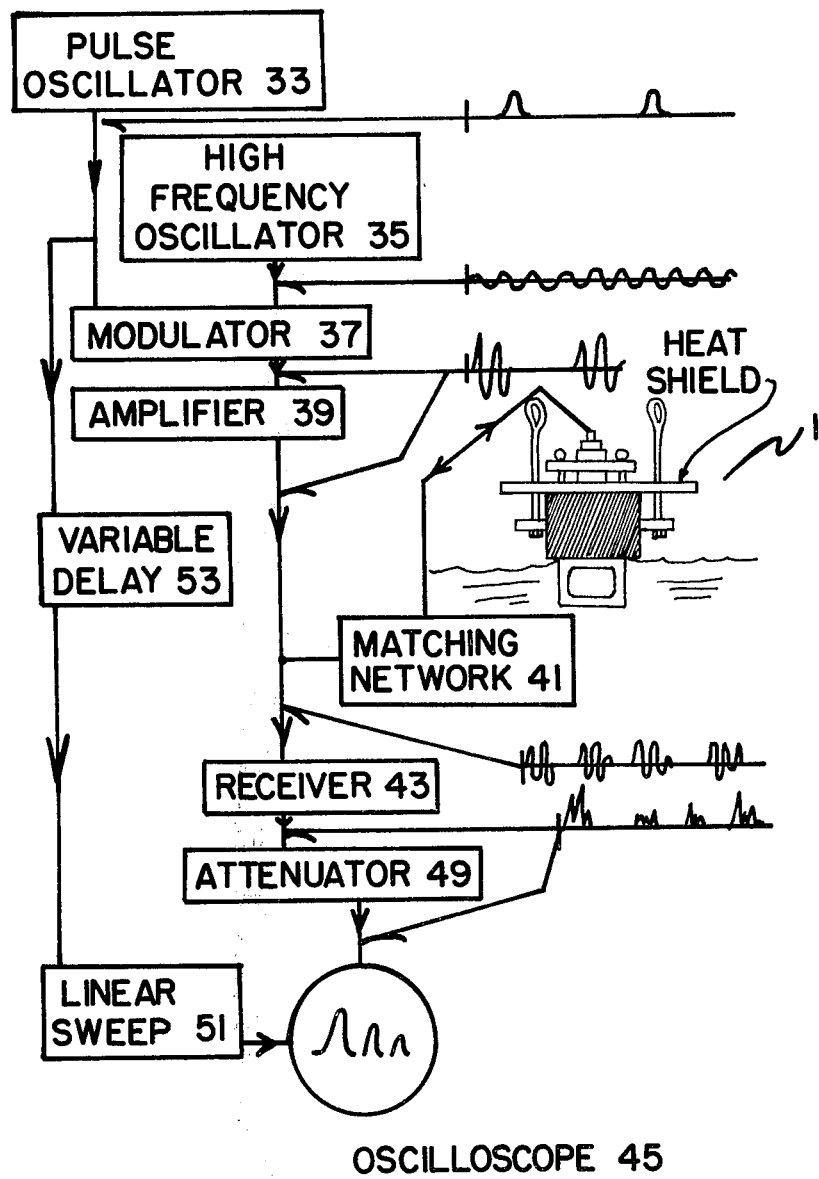
FIG. 3 is an exemplary circuit block diagram for operating the probe shown in FIGS. 1 and 2.

FIGS. 2 and 3 illustrate an improved probe 1 which is a presently preferred embodiment of this invention.

The probe 1 includes and comprises a body member 3 which is made essentially of titanium, and is preferably machined from a wrought titanium bar having a single phase structure. The body member 3 has opposite ends 5 and 7, each of which has a substantially flat end surface 9 which is substantially perpendicular to the longitudinal axis 11 of the body member 3.

A suitable piezoelectric transducer device 13 may be conveniently coupled to the surface 9 of body member end 7 by mechanical pressure applied against an O-ring 15 by a hold-down plate 17 as illustrated in FIG. 2. As shown, the plate 17 may be secured by a plurality of thumbscrews 19. To minimize acoustical resistance, a suitable coupling medium, e.g. a foil shim or a suitable high temperature oil or grease, should be interposed between the surface 9 of the body member end 7 and the working contact surface of the transducer device 13. For example, the coupling medium may consist of a suitable silicone compound such as Dow Corning Corporation's 710 silicone fluid (serviceable from 0° to 500° F.).

The transducer device 13 may be of any conventional type which operates within the desired ranges for frequency and power. Transducers which employ a crystal made of quartz, barium titanate or a suitable ceramic material may generally be used with the illustrated embodiment of this invention. For example, A-3000 series flat immersion type search units made by Panametrics, Inc. may be used.

Operability of a typical piezoelectric transducer is limited by its Curie point temperature. A transducer which uses a quartz crystal must usually be operated at temperatures of 300° C. or less, for example. A transducer which uses a barium titanate crystal must usually be operated at temperatures of 110° C. or less. Thus it will be important to cool the probe 1 such that the surface 9 of body member end 7 will have a temperature within the operating limit for the transducer device 13. The temperature of this surface 9 can be monitored using a thermocouple connected at hole 21 shown in FIG. 2.

The probe 1 has a working tip which is formed by the end 5 of the body member 3. To avoid undue attenuation of ultrasonic signals by the titanium probe material, the working tip should be relatively short. Thus, the working tip should have a length A which is about ⅛ to 3 inches preferably about ¼ to 2 inches, e.g. about ⅞ inches.

As shown, the body member 3 is defined in part by a lateral portion 29 adjacent the working tip, where the lateral portion 29 has a length B and defines a cooling zone for the probe 1. The length B should be relatively short, preferably about 2½ to 3 inches, to avoid undue attenuation of the ultrasonic signals while allowing sufficient surface area for the probe 1 to be adequately cooled.

Heat is extracted at the above-mentioned cooling zone by cooling means such as a water jacket 31 or the like. The water jacket 31, which may be made of brass and shrink fitted in place, should have the capacity to cool the probe 1 in a manner such that when its working tip reaches a thermal equilibrium upon being immersed in an aluminum melt at a temperature in the range of about 675° to 825° C., there exists a negative temperature gradient of at least 200° C./in, e.g. about 250° C./in, along the axis 11 within the probe cooling zone. This negative temperature gradient should reduce the probe temperature along the axis 11 from the point of immersion, e.g. point C, to a point where the probe temperature is 300° C. or less. This negative temperature gradient is necessary to avoid undue attenuation of low power ultrasonic signals by the titanium probe material. It should also be effective to reduce the temperature of the surface 9 of body member end 7 within the operating limit for the piezoelectric transducer device 13.

As shown in FIG. 2, the water jacket 31 may comprise a two piece assembly including a cap 22 which can be secured with silver solder. In the figure, the thumbscrews 19 pass through the transducer hold-down plate 17 and are threaded into the cap 22. As security against slippage between the probe lateral portion 29 and the water jacket 31 when the probe 1 is operated, an additional thumbscrew (not shown) may be passed through the hold-down plate 17 and threaded into the body member end 7.

The probe 1 may also include a substantially flat reflective surface 23 in opposed, spaced apart, substantially parallel relationship within the surface 9 of the end 5 of body member 3. As shown in FIG. 2, the reflective surface 23 may be spaced from the surface 9 by a pair of opposed support walls 25. Thus, the surface 9 of the end 5 defines a cavity 27 which is further defined by the support walls 25 and the reflective surface 23. The cavity 27 will fill with molten metal when the probe 1 working tip is immersed, and it will accommodate a molten metal flow when the working tip is immersed for inspecting a molten aluminum stream. If desired, the support walls 25, the reflective surface 23 and the body member 3 may all be made using a single piece of titanium bar stock in which the cavity 27 may be formed using a conventional machining operation.

The surface 9 of the end 5 and the reflective surface 23 may each measure about 2 inches by 2 inches square and are spaced apart by a distance D such that in operation ultrasonic signals transmitted from the surface 9 are reflected off of the reflective surface 23 and back to the surface 9 of end 5 after traveling a known reference distance. It is necessary to use a reflective surface, such as the surface 23, for purposes of detecting and evaluating velocity and comparative amplitude attenuation and frequency shifts of the ultrasonic signals. A reference reflective surface is not needed for discontinuity detection, however. It would, of course, be possible to omit the reflective surface 23 along with the support walls 25 and to utilize a suitable substitute reflective surface detached from the probe 1 and positioned within the aluminum melt. Part of the structure which contains the melt might be utilized, for example. However, the illustrated configuration greatly simplifies things by allowing the probe 1 to be installed and moved without having to worry about aligning the probe 1 or re-establishing the distance that the signals will travel.

The reflective surfaces 23 should be spaced at least about ½ inch from the surface 9 of the probe end 5. For example, a spacing distance D of about 1¼ to about 2 inches can be used. This assures a signal path through the melt that is of sufficient length so that characteristic data can be obtained. The spacing distance D should also be such that the ratio of the distance D to the probe length (A+B) is less than the ratio of the signal velocity through the melt to the average signal velocity through the probe (under operating conditions). This is to avoid the possibility of an overlap between the received signals from the melt and the second received reflection from the probe-melt interface.

To promote wetting, the probe working tip is desirably capped with a coating of aluminum which has been volatilized and deposited on the working tip in a vacuum. Upon the immersion of the working tip in an aluminum melt at temperatures up to about 850° C., the working tip is desirably wetted by molten aluminum in about one minute or less, e.g. about 15 seconds. Once it is wetted, when the probe working tip is removed from the liquid metal, exposed to the atmosphere and allowed to cool, and then re-immersed in the melt, rewetting should desirably occur in a similarly short time, e.g. in about one minute or less, and usually in about 15 seconds.

To achieve these wetting characteristics, the aluminum coating can conveniently be applied to the titanium probe working tip using the following process.

First, the working tip is chemically etched to clean and to remove titanium oxides and other reaction products from the working tip surface. This step may be carried out using a suitable acidic aqueous solution containing at least one acid selected from the group consisting of chromic acid, hydrofluoric acid, phosphoric acid, nitric acid, sodium sulfate and sulfuric acid. Satisfactory results have been obtained, for example, using a solution which consists essentially of about 20 wt.% hydrofluoric acid and about 30 wt.% nitric acid, balance water. Preferably, the etching step is continued until a sufficient amount of elemental titanium is removed from the probe working tip for the underlying titanium grain structure to become visible at the working tip surface.

The etched workpiece is then situated in a vacuum atmosphere preferably about 50 to 300 microns pressure, e.g. about 200 microns pressure, where the working tip surface is bombarded with ionized gas from a glow discharge preferably for a period of about 15 to 60 minutes, e.g. about 45 minutes. These steps further clean and remove titanium oxides and other reaction products from the working tip surface.

The vacuum atmosphere pressure is decreased preferably to about 0.005 to 0.5 microns pressure, e.g. about 0.01 microns pressure, and then aluminum is volatilized in the presence of the workpiece preferably for about 15 to 30 seconds, e.g. about 20 seconds, such that the volatilized aluminum is deposited on the working tip surface to form the desired coating.

To seal the coated probe working tip and to inhibit its oxidation, it is good practice to immerse the working tip in an aluminum melt within a few minutes after the probe is removed from the vacuum atmosphere. It may also be helpful to operate the probe at this time. Upon removing the probe from the melt, the probe may be allowed to cool and then stored.

The probe 1 can be operated using conventional pulse-echo circuitry which is well known in the art. U.S. Pat. No. 2,280,226 to F. A. Firestone discloses circuitry for a reflectoscope that can be used for example. A Model S-80 reflectoscope with a model PR-1 pulser/receiver made by Automation Industries, Inc. can be used with good results. Alternatively, a model 9000 attenuation comparator made by Matec, Inc. could be used.

An exemplary circuit block diagram for operating the probe 1 is illustrated in FIG. 3. As shown, outputs from a pulse oscillator 33 and a high frequency oscillator 35 are supplied to a modulator 37 which in turn supplies an output to amplifier 39. The resultant amplifier 39 output is a radio-frequency pulse of a few microseconds in duration at a repetition rate of between about 50 Hz to about 5000 Hz, e.g. about 2.5 KHz. The repetition rate of this r.f. pulse is not critical, but it should be sufficiently slow to prevent reflections from successive pulses from overlapping each other. The maximum pulse amplitude may be on the order of a few hundred to several thousand volts, but raising the voltage does not necessarily raise the sensitivity proportionately, and about 500 volts will work very well. The pulse carrier frequency should be on the order of what is required for molten aluminum inspection methods, e.g. 9.5 MHz, and will, of course, depend on the operating characteristics of the piezoelectric transducer 13.

The amplifier 39 output is supplied to the transducer 13 through an impedance matching network 41 which matches the transducer capacitance with an inductance for improved operating efficiency. In response to the amplifier 39 output, the transducer 13 sends out ultrasonic signals through the probe 1 and into the melt under inspection. Reflections of echoes of these signals are returned to the transducer 13. The transducer 13 converts the echoes to electrical energy which is supplied back through the matching network 41 to tuned receiver 43. The receiver 43 output is in turn supplied to an oscilloscope 45 through a variable signal attenuator 49. The oscilloscope 45 is synchronized by a connection of its linear sweep 51 to the pulse oscillator 33 through a variable delay 53.

Since the transmitted and the received pulses are both impressed upon the receiver 43, they are both readable simultaneously on the visual display of the oscilloscope 45. However, the delay 53 may be adjusted so that the transmitted pulses do not appear.

The attenuator 49 may be adjusted so as to regulate the amplitude of the displayed pulses and is useful for purposes of calibration. For example, when inspecting for discontinuities or insoluble particulate matter in the melt, it is useful for calibrating the display according to a distance-amplitude-correction curve for a known type and size defect such as a ¼ inch alumina ball.

Read out sensitivity for the received pulses can be adjusted by selection or adjustment of the transmitted pulse carrier frequency. Since sensitivity may vary according to the type of measurement that is being made, it is convenient to provide a variable control feature for the high frequency oscillator 35.

The probe 1 as thus described as a device which is well suited for monitoring and establishing the quality of molten aluminum in metal cleaning and casting operations. The device is simple, rugged, reliable and is adapted for use in an aluminum cast house on a daily, routine basis as a production quality control tool. It may be used to learn about or demonstrate the effect of some factor or variable in a process, to establish a quality level requirement for a particular process and product, or to compare quality in a given operation to previously established quality level criteria.

Using the probe 1, metal quality can be measured ultrasonically with respect to discrete particulate, with respect to changes in signal attenuation, and with respect to quality problems related to velocity changes or frequency changes. With the appropriate electronics and read-out devices, any of these quality measurements can be made singly, or in any combination desired, with a single probe in the molten metal.

As mentioned in reference to FIG. 3, the instantaneous state of quality of the metal in the probe cavity can be known through a display of the measuring characteristic or characteristics on a cathode ray tube. Alternatively or simultaneously, the signal or signals may be recorded. The recording can serve as an integrated measure of quality for the whole quantity of metal which flows through the probe, with any variation or problem of quality becoming known on a time scale extending for a complete operation.

To measure or record metal quality at several locations, multiple probes can be used, or a single probe can be shifted among location since there is no appreciable delay in the functioning of a probe either when it is first put into use or when it is shifted from one position to another.

While this invention has been described with reference to particular embodiments thereof, it will be recognized that numerous embodiments of the invention are possible, and that the invention is to be defined and limited only by the scope of the following claims.

What is claimed is:

1. An improved probe for conducting ultrasonic mechanical energy to and from an aluminum melt in a process of inspecting molten aluminum, where said probe comprises:
   (a) A body member made essentially of titanium and having first and second opposite ends, each of which has a substantially flat end surface which is substantially perpendicular to the longitudinal axis of said body member, where said first end forms a working tip for said probe, said working tip being about ⅛ to 3 inches in length, said body member being further defined by a lateral portion adjacent said working tip, where said lateral portion defines a cooling zone for said probe; and (b) Cooling means, such as a water jacket or the like, for extracting heat at said cooling zone to cool said probe, where said cooling means has the capacity to cool said probe in a manner such that when said working tip reaches a thermal equilibrium upon being immersed in an aluminum melt at a temperature in the range of about 675° to 825° C., there exists a negative temperature gradient of at least 200° C./in along the longitudinal axis of said body within said cooling zone, and the temperature of said second end of said body member is maintained at 300° C. or less.

2. An improved probe according to claim 1 including a substantially flat reflective surface in opposed, spaced apart substantially parallel relationship with said substantially flat end surface of said first end of said body member which forms said working tip.

3. An improved probe according to claim 2 wherein said substantially flat end surface of said first end of said body member and said substantially flat reflective surface each measure about 2 inches ×2 inches square and are spaced apart by about 1½ to 2 inches.

4. An improved probe according to claim 3 wherein said cooling zone is about 2½ to 3 inches in length.

5. An improved probe according to claim 1 wherein said substantially flat end surface of said first end of said body member which forms said working tip defines a portion of a cavity, where said cavity is further defined by a substantially flat reflective surface in opposed, spaced apart substantially parallel relationship with said substantially flat end surface of said first end of said body member.

6. An improved probe according to claim 1 wherein a piezoelectric ultrasonic transducer is coupled against said substantially flat end surface of said second end of said body member.

7. An improved probe according to claim 6 wherein said cooling means has the capacity to cool said probe in a manner such that when said working tip reaches a thermal equilibrium upon being immersed in an aluminum melt at a temperature in the range of about 675° to 825° C., the temperature of said second end of said body member is maintained below the Curie point of said transducer.

* * * * *